(12) United States Patent
Gopalakrishnan et al.

(10) Patent No.: US 9,002,875 B2
(45) Date of Patent: Apr. 7, 2015

(54) METHOD FOR OPTIMIZING CLINICAL DATA STANDARDIZATION

(76) Inventors: Kalyan Gopalakrishnan, East Windsor, NJ (US); Ram Yeleswarapu, Bridgewater, NJ (US); Balendra Latupalli, Monmouth Junction, NJ (US)

( * ) Notice: Subject to any disclaimer, the term of this patent is extended or adjusted under 35 U.S.C. 154(b) by 706 days.

(21) Appl. No.: 12/739,815

(22) PCT Filed: Oct. 27, 2008

(86) PCT No.: PCT/US2008/081324
§ 371 (c)(1),
(2), (4) Date: Jul. 29, 2010

(87) PCT Pub. No.: WO2009/055790
PCT Pub. Date: Apr. 30, 2009

(65) Prior Publication Data
US 2010/0299335 A1    Nov. 25, 2010

Related U.S. Application Data

(60) Provisional application No. 60/982,737, filed on Oct. 26, 2007.

(51) Int. Cl.
*G06F 17/30* (2006.01)
*G06F 19/00* (2011.01)

(52) U.S. Cl.
CPC ........ *G06F 19/363* (2013.01); *G06F 17/30569* (2013.01); *G06F 19/322* (2013.01)

(58) Field of Classification Search
CPC .......... G06F 17/2247; G06F 17/30067; G06F 17/30286; G06F 17/30569; G06F 17/30595; G06F 17/30961
USPC .......................................................... 707/756
See application file for complete search history.

(56) References Cited

U.S. PATENT DOCUMENTS

| 6,507,829 B1 | 1/2003 | Richards et al. | |
| 6,799,184 B2 * | 9/2004 | Bhatt et al. | 707/718 |
| 8,683,435 B2 * | 3/2014 | Richards et al. | 717/121 |

FOREIGN PATENT DOCUMENTS

JP    2004-348271    12/2004

OTHER PUBLICATIONS

Kush, "Electronic Data Capture—Pros and Cons", BioExecutive International, Supplement Series, Jun. 2006, pp. 48-52.*
CDISC SDTM Implementation Guide (SDS Version 3.1), CDISC, Jul. 14, 2005.*
International Search Report and Written Opinion issued for PCT/US08/81324 on Mar. 31, 2009.

* cited by examiner

*Primary Examiner* — Robert Beausoliel, Jr.
*Assistant Examiner* — Nirav K Khakhar
(74) *Attorney, Agent, or Firm* — Fox Rothschild LLP; Richard C. Woodbridge; Ryan N. North

(57) ABSTRACT

A method of integrating clinical trial data into a form required by a standards based data format. Annotations may be made to a case report form (CRF) designed for a clinical trial that map report form data to standards compliant data. The annotations may be stored in, and then applied to data captured using that particular case report form to produce standards compliant data for that particular clinical trial. The data sets produced may then be validated as being standards compliant.

12 Claims, 3 Drawing Sheets

METHOD FOR OPTIMIZING CLINICAL DATA STANDARDIZATION

CROSS REFERENCE TO RELATED APPLICATIONS

This application is a 371 National Phase Application of PCT/US08/81324 filed Oct. 27, 2008. PCT/US08/81324 is related to, and claims priority from, U.S. Provisional Patent application No. 60/982,737 filed on Oct. 26, 2007, by Kalyan Gopalakrishnan entitled "Process for Optimization for Clinical Data Standardization", the contents of both applications are hereby incorporated by reference.

FIELD OF THE INVENTION

The present invention relates to methods for gathering and storing data, and more particularly, to methods for transforming data gathered in clinical trials into regulatory compliant formats.

BACKGROUND OF THE INVENTION

In the US, and most other industrial countries, pharmaceuticals are strictly regulated by government agencies such as the US Food and Drug Administration (FDA). Part of this regulation requires that pharmaceutical and medical companies conduct extensive clinical research in order to demonstrate the safety and efficacy of new drugs and devices before they can be approved for commercial use.

These clinical trials are typically costly and time consuming and usually involve significant amounts of data. In order to speed up, and reduce the cost of, clinical trials and their evaluation, the FDA is attempting to implement standardization of the data that is electronically submitted to them as regulatory submissions for evaluation.

In particular, they are attempting to standardize on the Clinical Data Interchange Standards Consortium (CDISC)'s Study Data Tabulation Model (SDTM).

A problem facing the pharmaceutical and medical industry is that currently clinical, non-clinical, lab and healthcare data exists in multiple physical formats, with datasets typically having heterogeneous syntax and semantics. The data may also be located across multiple geographical locations and organizations, and may exist at different stage of the clinical research life cycle. All of these factors make it difficult to assemble and aggregate such data for regulatory submissions.

SUMMARY OF THE INVENTION

Briefly described, the invention provides a method of integrating clinical trial data into a form required by a standards based data format.

In a preferred embodiment, the method includes using a case report form (CRF) designed for a clinical trial. Typically such a CRF is designed to optimize data collection in a particular clinical trial, including not collecting unnecessary data while collecting all necessary data. The CRF is also typically designed to make the data collection as easy and accurate as possible for personal administering the clinical trial and may, therefore, include syntax and semantics that are not directly compliant with the standards requirements.

The trial CRF may be annotated with one or more annotations that map report form data to standards compliant data. For instance, a CRF in a particular clinical trial may have as one of the options for the outcome "Death". The standard may, however, stipulate that such an outcome be recorded as "Fatal". The annotation, in such a case, may be a metadata entry that automatically transforms any occurrence of that variable as "death" to "fatal".

The annotations may then be stored in, for instance, a metadata repository or other storage module. These stored annotations may then be applied to data that was captured in a clinical trial data using that particular case report form to produce standards compliant data for that trial.

One exemplary data standard that may be mandated by the US Food and Drug Administration for electronic data submission is the Clinical Data Interchange Standards Consortium (CDISC)'s Study Data Tabulation Model (SDTM).

In a further preferred embodiment, the data sets produced are validated as being standards compliant.

These and other features of the invention will be more fully understood by references to the following drawings.

DETAILED DESCRIPTION

A preferred embodiment of the invention will now be described in detail by reference to the accompanying drawings in which, as far as possible, like elements are designated by like numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

Figure 1:
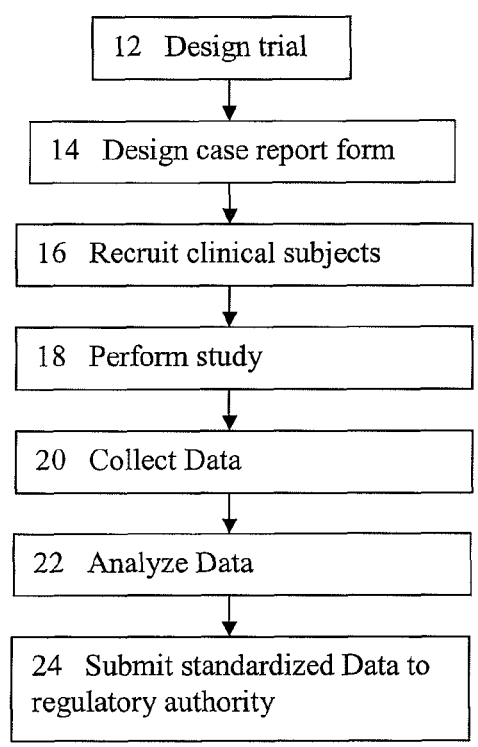
FIG. 1 is a schematic flow diagram of selected steps in an exemplary clinical trial.

FIG. 1 is a schematic flow diagram of selected steps in an exemplary clinical trial 10. In a typical first step 12, a clinical trial is designed. This may, for instance, be initiated by a sponsor or investigator that has identified a medication or device to be tested, typically termed the new agent, in the clinical trial. Usually, one or more pilot experiments are conducted prior to the clinical trial 10 to gain insights for the design of the clinical trial 10. The sponsor typically first decides what to compare the new agent to. They may, for instance, decide to compare the new agent to one or more existing treatments or a placebo or some combination thereof. Decisions are also made as to what kind of patients might benefit from the medication/device that is the new agent. These decisions are typically made in coordination with a panel of expert investigators such as, but not limited to, physicians well-known for their publications and clinical experience.

Once the clinical trial protocol has been designed, a Case Report Form (CRF) is designed in step 14. The CRF may be used in the clinical trial to collect the specific data needed in order to test the efficacy of the new agent in the clinical trial.

The CRF may be a paper or electronic research questionnaire, or some combination thereof. A well designed CRF may capture all the data necessary for the purpose of the clinical trial without additional data. Clinical trials are expensive, so collecting all the necessary data that may enable a successful clinical trial is typically a goal when designing a CRF. Collecting unnecessary data, or data that may not be analyzed in assessing the clinical trial, may slow down the clinical trial by unnecessary data processing. CRF's may, therefore, be a document that is unique to a specific clinical trial, and may, for instance, contain terminology specific to a particular area of medicine or particular treatment. A CRF may range in size and complexity from a handwritten one-time 'snapshot' of a patient's physical condition to hundreds of pages of electronically captured data obtained over a period of weeks or months.

Once a CRF has been successfully designed and produced, a typical next step in a case study is step 16 of recruiting clinical subjects. If a sponsor cannot obtain enough patients with the specific disease or condition relevant to the case study at one location, then investigators at other locations who can obtain the same kind of patients to receive the treatment may be recruited into the study.

Having recruited suitable clinical subjects, a clinical trial typically then takes step 18 of performing the study. This typically takes the form of administering the treatment(s), i.e., providing the new agent to the clinical subjects in the manner laid out in the clinical trial protocol.

In step 20, the data is collected typically using the CRF. These data may, for instance, include measurements like vital signs, amount of study drug in the blood, and whether the patient's health gets better or not.

In step 22 the data is analyzed. This is typically done by the sponsor of the clinical trial. Once the data has been analyzed and organized, it may be submitted to the appropriate regulatory authority in step 24.

Regulatory authorities such as, but not limited to, the US Food and Drug Administration (FDA) are the bodies whose responsibilities typically include protecting the public health by assuring the safety and efficacy of human and veterinary drugs and medical devices. The regulatory authorities typically access the data from the clinical trials and may use them to make decisions on whether or not to allow the drug to be used by the medical community and the public and may also decide on conditions of that use. In order to make these decisions more efficiently, regulatory authorities are typically requiring that the data submitted to them in step 24 is in a prescribed, standardized data format.

The US FDA has, for instance, begun mandating that clinical trial data submitted to them conform to the Clinical Data Interchange Standards Consortium (CDISC) Study Data Tabulation Model (SDTM). The CDISC is a non-profit organization, whose mission is to develop and support global, platform-independent data standards that enable information system interoperability to improve medical research and related areas of healthcare. Their CDISC SDTM is written in XML Schema.

SDTM is built around the concept of observations collected about subjects who participated in a clinical study. Each observation can be described by a series of variables, corresponding to a row in a dataset or table. Each variable can be classified according to its Role. A Role determines the type of information conveyed by the variable about each distinct observation and how it can be used. Variables may be classified into five major roles:

1. Identifier variables, which identify, for instance, the study, subject of the observation, the domain, and the sequence number of the record.

2. Topic variables, which specify the focus of the observation, such as, but not limited to, the name of a lab test.

3. Timing variables, which describe the timing of the observation, such as, but not limited to, start date and end date.

4. Qualifier variables, which include additional illustrative text, or numeric values that describe the results or additional traits of the observation, such as, but not limited to, units or descriptive adjectives.

5. A Rule that may express an algorithm or executable method to, for instance, define start, end, or looping conditions in the Trial Design model.

Figure 2:
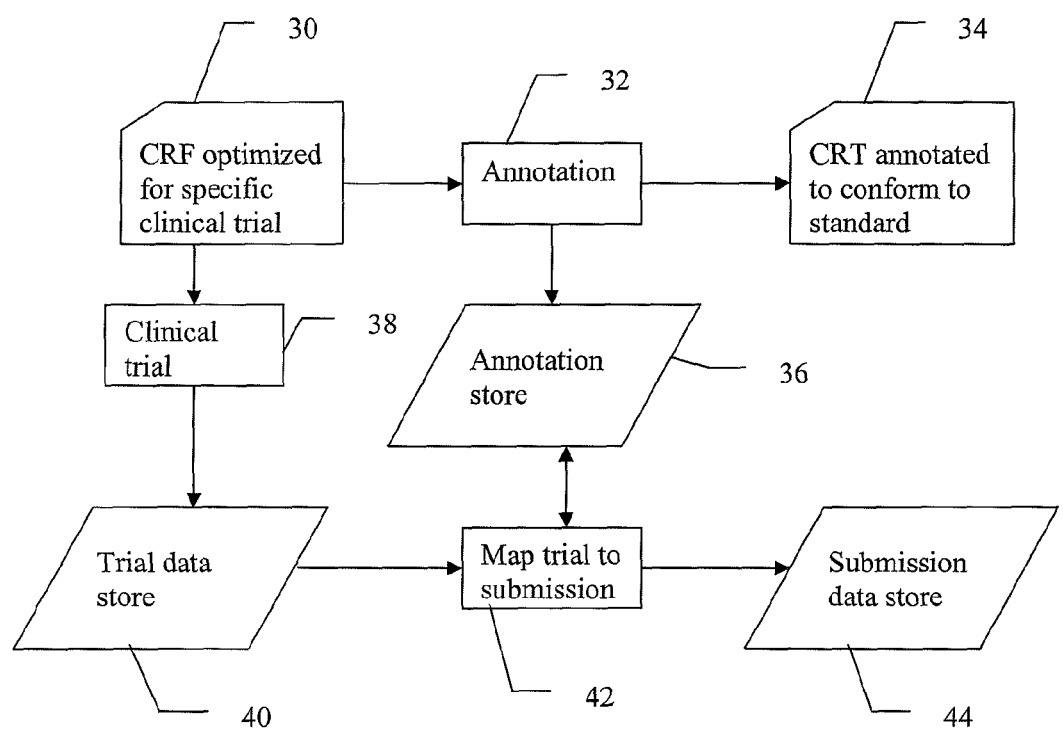
FIG. 2 is a schematic view of an exemplary embodiment of the present invention of integrating clinical trial data into a format suitable for submission to a regulatory agency.

FIG. 2 is a schematic view of an exemplary method of the present invention of integrating clinical trial data into a format suitable for submission to a regulatory agency 31. Integrating clinical trial data into a format suitable for submission to a regulatory agency 31 may be accomplished using a CRF optimized for a specific clinical trial 30. The CRF optimized for a specific clinical trial 30 may be a paper form or an electronic form, or some combination thereof.

The CRF optimized for a specific clinical trial 30 may be converted into a CRF annotated to conform to a standard 34 by a process of annotation 32. The standard that the CRF annotated to conform to a standard 34 conforms to may, for instance, be, but is not limited to, the CDISC SDTM standard model supported by the FDA's electronic submission process. In the annotation 32 process, both the format and terminology of the CRF optimized for a specific clinical trial 30 may be conformed to the CDISC SDTM standard model. For instance, the term "DIED" may be used to describe a trial outcome where the accepted CDISC SDTM standard model terminology is "FATAL".

The annotation 32 may, for instance, be accomplished using an electronic or e-CRF version of the CRF optimized for a specific clinical trial 30. The annotation 32 may be done by one or more skilled personal, or by one or more skilled personal augmented by suitable software, including, but not limited to, third party drag and drop tools and a resident standards metadata library that may be used for validation of the annotations. The software may, for instance, run on a general purpose server.

The annotations used to accomplish the annotation process may be stored in an annotation store 36. The annotation store 36 may, for instance, be a data storage device that is internal to the general purpose server running the annotation support software. The data stored in the annotation store 36 may, for instance, be metadata or XML metadata related to the CRF optimized for a specific clinical trial 30.

The CRF optimized for a specific clinical trial 30 may be used in a clinical trial 38. The data collected in the clinical trial 38 may be stored in a trial data store 40. The trial data store 40 may, for instance, be any suitable data storage device.

Once there is data in the trial data store 40, it may be mapped into data suitable for submission to a regulatory agency. A mapping of trial data to submission data process 42 may be done by suitable software running on a server that has access to the annotation data stored in the annotation store 36. Once trial data has been mapped or transformed into data suitable for submission to the regulatory agency, the data may be stored in a submission data store 44.

Figure 3:
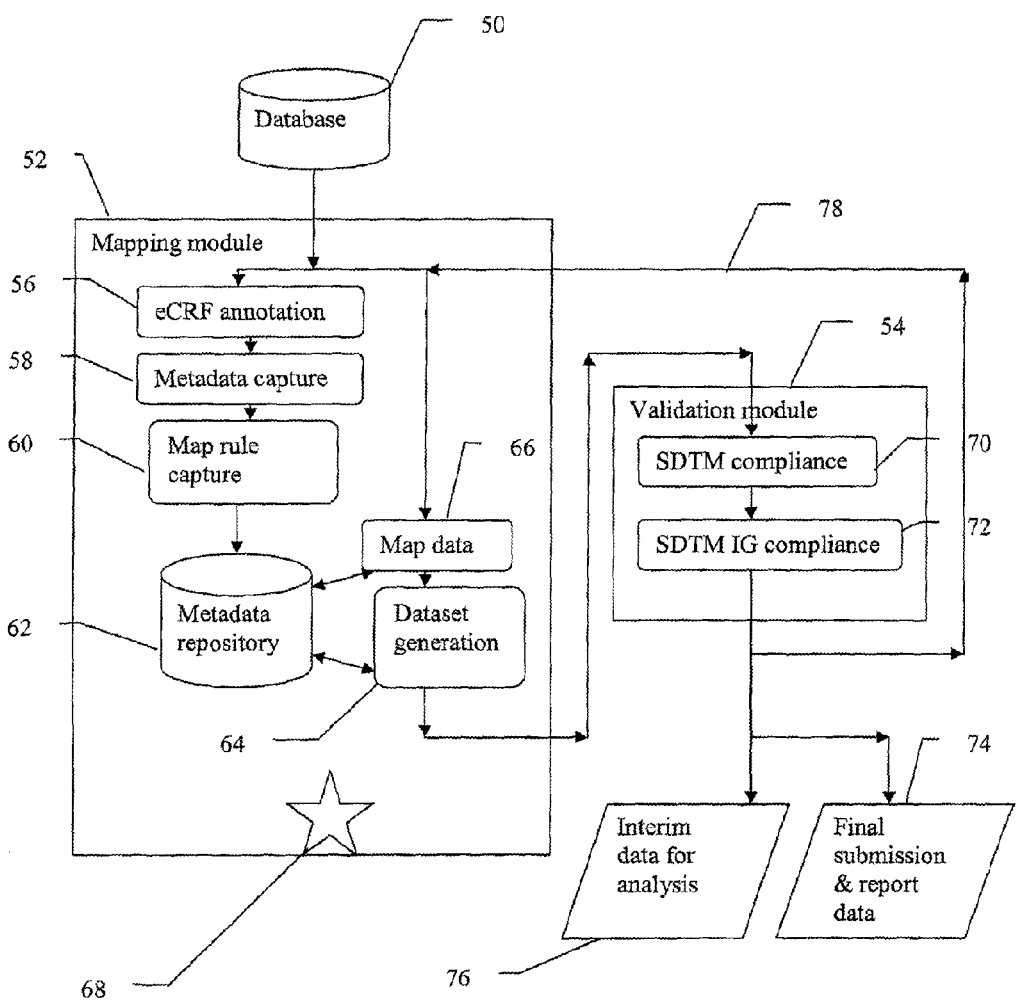
FIG. 3 is a schematic view of a further exemplary embodiment of the present invention of integrating clinical trial data into a format suitable for submission to a regulatory agency.

FIG. 3 is schematic view of a further exemplary embodiment of the present invention 51 of integrating clinical trial data into a format suitable for submission to a regulatory agency. The further exemplary embodiment of the present invention 51 includes a main database 50, a mapping module 52 and a validation module 54.

The mapping module 52 includes a eCRF annotation module 56, a metadata capture module 58, a mapping and transformation rule capture module 60, a metadata repository 62, a dataset generation module 64, a data mapping module 66 and a rules engine 68.

The validation module 54 includes a SDTM compliance module 70 and an SDTM IG compliance module 72.

The main database 50 may store raw data from current or historical clinical trials. The mapping module 52 may include one or more software programs running on one or more general purpose computers may be designed to take the raw data from the clinical data and convert the syntax and or semantics associated with the raw data into a form that is in compliance with a standard form such as, but not limited to, the CDISC STDM standard or the ADaM standard. The eCRF annotation module 56 facilitates and captures annotations to the CRF used to gather data in the clinical trial dataset being analyzed. This may involve computerized augmentation of an operator's interaction with an electronic version of the original CRF used in the clinical trial. The metadata capture module 58 may, for instance, capture the metadata associated with such annotations. The mapping and transformation rule capture module 60 facilitates and captures mapping and transformation rules for converting the data set captured in the clinical trial into a standards compliant format, syntax and semantics.

The captured data may be validated in real-time using, for instance, a metadata library that may, for instance, be stored in the metadata repository 62.

The metadata repository 62 may be a general purpose, electronic data storage device that may be used to store the mapping and transformation rules captured by the mapping and transformation rule capture module 60, as well as the metadata captured by the metadata capture module 58 and the annotations captured by the eCRF annotation module 56.

The data mapping module 66 uses the mapping and transformation rules, metadata and annotations stored in the metadata repository 62 to map the raw trial data into standards compliant data. For data to be submitted electronically to the US FDA this standard is typically the CDISC STDM.

The dataset generation module 64 takes the data that has been source-to-target mapped by the data mapping module 66 and generates the data sets in standard complaint form.

The interaction of the various modules of the mapping module 52 may be managed and controlled by a rules engine 68.

The validation module 54 typically validates the generated data for compliance with the required standards. For the CDISC STDM, this may include validation against the standards model by a SDTM compliance module 70 as well as against the standards Implementation Guidelines (IG) by a SDTM IG compliance module 72.

The output standardized and validated data may become interim data for analysis 76 or final submission and report data 74. The data may also be feed back by a data feed back path 78 to the mapping module 52. The feed back data may, for instance, be used to further refine the annotations, metadata and mapping rules.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

Modifications may readily be devised by those ordinarily skilled in the art without departing from the spirit or scope of the present invention.

What is claimed is:

1. A method of integrating clinical trial data into a form required by a standard, said method comprising:
   providing a case report form designed to capture specific data needed to test the efficacy of a new agent in a clinical trial;
   capturing the specific data, wherein the specific data that has been captured is stored in a trial data store and at least a portion of the stored specific data is in a non-compliant format that includes at least one data variable element that varies in at least one of a format, syntax, and semantics;
   analyzing, by a data mapping processor, the specific data stored that is in the non-compliant format in the trial data store to capture transformation rules capable of converting the at least one variable data element into at least one standards compliant data element that does not vary in format, syntax, and semantics;
   converting, by the data mapping processor, the specific data that is in the non-compliant format into a standards compliant format, wherein said converting applies said transformation rules that transform the at least one variable data element into the at least one standard data element;
   validating said standards complaint data to generate validated submission data; and
   storing said validated submission data in a submission data store.

2. The method of claim 1 wherein said specific data further comprises metadata.

3. The method of claim 2 wherein said standards compliant data and metadata comprises an XML data format.

4. The method of claim 2 wherein said standards compliant data and metadata comprises a Clinical Data Interchange Standards Consortium (CDISC) Study Data Tabulation Model (SDTM).

5. The method of claim 1 wherein said validated submission data is suitable for submission to a regulatory agency.

6. The method of claim 5 wherein said regulatory agency is the US Food and Drug Administration (FDA).

7. The method of claim 1 wherein said standards compliant validated submission data is generated by validating said standards compliant data using a standards model.

8. The method of claim 7 wherein said standards model is a Clinical Data Interchange Standards Consortium (CDISC) Study Data Tabulation Model (SDTM).

9. The method of claim 1 further comprising the step of verifying said annotations using a standards interpretation guide.

10. The method of claim 6 wherein said standards interpretation guide is a Clinical Data Interchange Standards Consortium (CDISC) Study Data Tabulation Model Implementation Guide (SDTMIG).

11. The method of claim 5, further comprising submitting said validated submission data to the regulatory agency.

12. A system for integrating clinical trial data into a form required by a standard, said system comprising:
   a case report form designed to collect specific data needed to test the efficacy of a new agent in a clinical trial;
   a database for storing the specific data, wherein the database includes:
      a trial data store for capturing and storing said specific data in which at least a portion of the stored specific data is in a non-compliant format that includes at least one variable data element that varies in at least one of a format, syntax, and semantics, and a submission data store for storing validated submission data;

a data mapping processor connected to said database and configured to:

analyze the specific data stored in the trial data store, to capture transformation rules capable of converting the at least one variable data element into at least one standards compliant data element that does not vary in format, syntax, and semantics, and convert the specific data into a standards compliant format by applying said transformation rules that transform the at least one variable data element into the at least one standard data element;

a validation module connected to said data mapping processor configured to validate said standards compliant data; and a dataset generation module configured to generate validated submission data based on said standards compliant data.

* * * * *